(12) United States Patent
Dupont

(10) Patent No.: US 6,927,058 B1
(45) Date of Patent: Aug. 9, 2005

(54) TELLTALE SANITARY GASKET

(75) Inventor: Paul Robert Dupont, Blairstown, NJ (US)

(73) Assignee: Rubber-Fab, Inc, Andover, NJ (US)

( * ) Notice: Subject to any disclaimer, the term of this patent is extended or adjusted under 35 U.S.C. 154(b) by 18 days.

(21) Appl. No.: 10/837,844

(22) Filed: May 3, 2004

(51) Int. Cl.$^7$ ................................................ C12M 1/34

(52) U.S. Cl. .................. 435/287.4; 435/288.7; 435/808; 422/58; 422/82.05; 277/317; 277/602; 277/910

(58) Field of Search ................ 435/287.4, 288.7, 435/808; 422/58, 82.05; 277/317, 602, 910

(56) References Cited

U.S. PATENT DOCUMENTS 5,872,004 A * 2/1999 Bolsen .................... 435/287.4

* cited by examiner

Primary Examiner—David Redding
(74) Attorney, Agent, or Firm—Howard R. Popper

(57) ABSTRACT

A gasket for use with sanitary piping systems contains a receptacle for retaining an encapsulated bacterial test indicator. The receptacle has a length that permits the indicator end of the test indicator to be directly exposed to the sterilizing steam that is introduced into the piping system. The gasket is preferably installed at the sanitary flange of a short "bull" T-section of the stainless steel sanitary piping and secured thereto by a stainless steel cap. The stainless steel cap is recessed to accommodate as much of the test indicator length as may be required to position the indicator end of the test indicator in the central lumen of smaller pipe diameters.

8 Claims, 1 Drawing Sheet

TELLTALE SANITARY GASKET

FIELD OF THE INVENTION

This invention relates to sanitary piping systems and, more particularly, to apparatus for ensuring that the sterility of the piping system.

BACKGROUND OF THE INVENTION

To verify the degree of sterility obtaining in an autoclave process it has been conventional practice to insert into the autoclave a bacterial indicator, such as shown in any of U.S. Pat. No. 6,623,955; 5,252,484; or 5,418,167. After the autoclave heating cycle has run its course, the bacterial indicator is place in an incubator to determine whether the autoclaving has been successful in killing the bacteria in the test indicator.

However, to assess the sterility of sanitary piping and tank systems used for food processing, the practice has been to insert a thermocouple wrapped with a bacterial test strip into the system. Sterilizing steam is applied and maintained at an appropriate temperature for a specified length of time. After the steam is turned off the test strip is removed and incubated to see if the bacteria in the test strip have been killed by the steam. If all goes well and the test strip has not become dislodged from the thermocouple, the conventional process takes approximately seven days during which time the piping system cannot be put to productive use.

It would be extremely advantageous to be able to use the encapsulated bacterial indicator of the aforementioned patents in sanitary piping, tank systems and fermenters in order to reduce the time taken to verify the sterility of the sanitary piping systems.

SUMMARY OF THE INVENTION

In accordance with the principle of the present invention, in one preferred embodiment thereof, a gasket having contours to meet the contours of a conventional sanitary flange contains a receptacle for retaining an encapsulated bacterial test indicator. The receptacle has a length that permits the indicator end of the test indicator to be directly exposed to the sterilizing steam that is introduced into the piping system. The gasket is preferably installed at the sanitary flange of a short "bull" T-section of the stainless steel sanitary piping and secured thereto by a stainless steel cap. The stainless steel cap is recessed to accommodate as much of the test indicator length as may be required to position the indicator end of the test indicator in the central lumen of smaller pipe diameters.

BRIEF DESCRIPTION OF THE DRAWING

The foregoing and other objects of the present invention may become more apparent from a reading of the ensuing description together with the drawing, in which.

GENERAL DESCRIPTION

Figures 1, 3, 4:
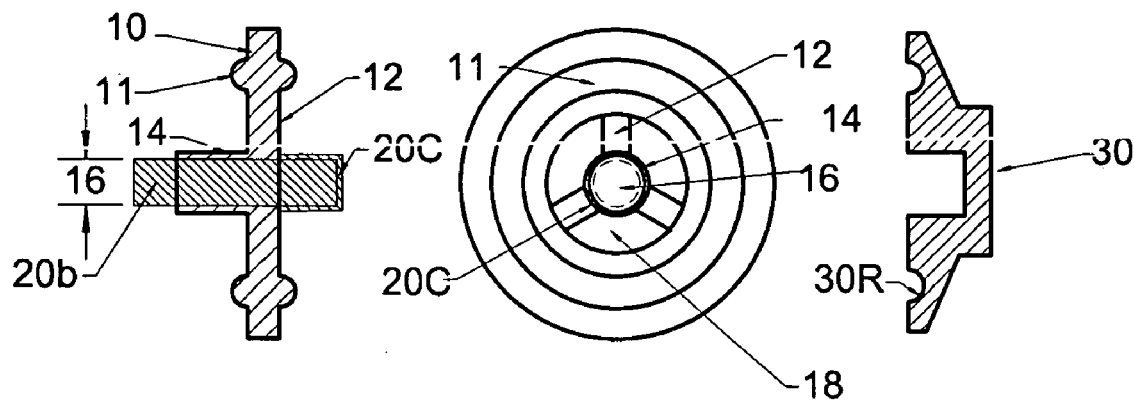
FIG. 1 shows a side view of the encapsulated bacterial test indicator of the aforementioned prior art patents.
FIG. 3 shows a plan view of the sanitary gasket of the invention.
FIG. 4 shows a side view of the sanitary cap for securing the gasket to a sanitary pipe flange.

Referring to FIG. 1, the bacterial test indicator 20 of the aforementioned prior art patents is shown having a test and 20b and a cap end 20c. The test end 20b is adapted to be permeable by a sterilizing stream of steam or other sterilizing agent such as ethylene oxide. As commercially available, the indicator end is normally colored blue. The cap end 20c fits over the main body of the indicator and secures its contents. Further and other details of this device may be obtained from any of the aforementioned patents which are hereby incorporated by reference.

Figure 2:
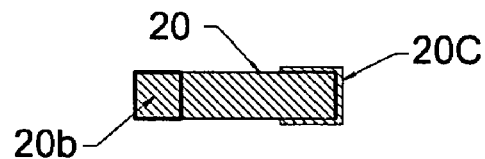
FIG. 2 show a sectional view of the inventive sanitary gasket having the test indicator installed.

FIG. 2 shows the gasket 10 of the invention which has a raised ring 11 designed to fit into the "O-ring" indentation of a standard sanitary flange fitting. An example of a prior art sanitary flange fittings is shown in prior art patents such as U.S. Pat. No. 2,789,844. In addition to the flange sealing ring portion 11, gasket 10 includes a central cylindrical container 14 having an inside diameter 16 (see FIG. 3) dimensioned to accommodate, with a slight friction fit, the main body of indicator 20, 20b. However, the diameter 16 is small enough to prevent the cap portion 20c from slipping through. Accordingly, the cap 20C is supported by gasket 10. As shown more clearly in FIG. 3, the central cylindrical container 14 is connected to the main body of gasket 10 and advantageously supported thereby with three equally-spaced ribs 12 which will allow the sanitizing steam to pass through and around the bacterial test indicator 20.

FIG. 4 shows a section through the cap 30 which includes an "O-ring" recess 30R to accommodate the O-ring portion 11 of gasket 10. The central portion of cap 30 includes a major recess dimensioned to accommodate the cap portion 20C of bacterial test indicator 20.

Figure 5:
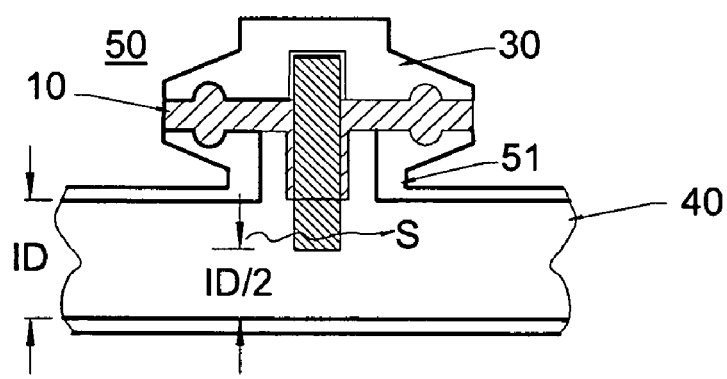
FIG. 5 shows the gasket and cap of the invention installed on a short bull T-section of sanitary piping.

As shown in FIG. 5, the gasket of the invention is preferably to be used in connection with a short "bull" T-section 50 having a major ID to accommodate the main flow of sanitizing steam for the sanitary piping system being sterilized. The T-section is equipped with a sanitary flange 51 onto which the inventive gasket 10 is positioned with the bacterial test indicator in place. As shown in FIG. 5, the T-section is advantageously to be dimensioned so that with the gasket 10 and indicator 20 in place and secured by cap 30, the end portion 20b of indicator 20 shall be exposed to the main flow S of sanitizing steam. In addition, the central portion of cap 30 is dimensioned with sufficient depth to allow the test indicator to be adjusted so that its central portion 20b will be in the central portion of the major ID of the T-section. In this manner the steam S can penetrate the apertures (not shown) of portion 20b to interact with the indicator materials therein.

Illustrative embodiments of the present invention have been fabricated using gasket made of steam-stable materials such as platinum silicone, EPDM and E. I. duPont's fluoroelastomer VITON®. Although the illustrative embodiment has been described using steam as the sanitizing agent for a sanitary piping system, it will be apparent to those skilled in the art that sanitary piping systems include tanks and fermenter systems. It should also be apparent that, in addition to the type of biological indicator thus far described which are used with steam, similar biological indicators are available for use when ethylene oxide is the sanitizing agent.

Further and other modifications of the illustrative embodiment may be apparent to those skilled in the art and may be made without, however, departing from the spirit and scope of the invention.

What is claimed is:

1. A tell tale gasket for a sanitary piping system, comprising
- a main body portion having an O-ring section for mating with a sanitary flange;
- a centrally supported receptacle dimensioned to accommodate the minor diameter of a bacterial test indicator; said test indicator having a larger diameter cap end and an indicator end;
- ribs connecting said receptacle to said main body, said ribs permitting said steam to flow about said sanitary indicator;
- said receptacle having an axial length short enough to permit said indicator end to protrude beyond the end of said receptacle, whereby steam entered into said piping system may penetrate into said indicator end.

2. In combination,
- a sanitary piping T-section having at least one sanitary flange, the main diameter of said T-section being part of a sanitary piping system to which a sanitizing fluid is to be admitted;
- a gasket for fitting to said sanitary pipe flange, said gasket having a centrally supported receptacle portion for snugly accommodating the minor diameter of a bacterial test indicator having a larger diameter cap end and an indicator end, said receptacle having an axial length to permit said indicator end to protrude beyond the end of said receptacle; and
- a sanitary cap fitting for mating with said gasket to secure said gasket to said T-section flange, said cap being dimensioned to position said indicator end in the central portion of said T-section main diameter thereby exposing said indicator end to the main flow of said sanitizing fluid.

3. The combination of claim 2 in which said sanitizing fluid is steam.

4. A sanitary gasket, comprising,
  a. an O-ring portion for mating with a sanitary flange of a piping system;
  b. a retainer cup for accommodating an encapsulated bacterial test indicator; and
  c. a spider portion for supporting said retainer cup in a central lumen of said piping system.

5. A sanitary gasket according to claim 4, wherein said retainer cup frictionally retains said encapsulated bacterial test indicator.

6. A sanitary gasket according to claim 5, wherein said encapsulated bacterial test indicator includes a cap, and wherein said retainer cup includes a minor diameter smaller than the diameter of said cap.

7. A sanitary gasket according to claim 5, wherein said spider portion includes passages facilitating the passage of steam toward said encapsulated bacterial test indicator.

8. A sanitary gasket according to claim 5, wherein said gasket is selected from steam-stable materials consisting of platinum silicone, EPDM and fuoroelastomer.

* * * * *